United States Patent
Park et al.

(10) Patent No.: US 9,687,384 B2
(45) Date of Patent: Jun. 27, 2017

(54) SLIDING-TYPE APPARATUS FOR THERMOTHERAPEUTIC TREATMENT

(75) Inventors: Ji Hoon Park, Chungcheongnam-do (KR); Hea Sung Lee, Chungcheongnam-do (KR)

(73) Assignee: CERAGEM CO., LTD. (KR)

( * ) Notice: Subject to any disclaimer, the term of this patent is extended or adjusted under 35 U.S.C. 154(b) by 323 days.

(21) Appl. No.: 14/130,178

(22) PCT Filed: Jun. 11, 2012
(Under 37 CFR 1.47)

(86) PCT No.: PCT/KR2012/004609
§ 371 (c)(1),
(2), (4) Date: Apr. 7, 2014

(87) PCT Pub. No.: WO2013/002498
PCT Pub. Date: Jan. 3, 2013

(65) Prior Publication Data
US 2016/0038335 A1 Feb. 11, 2016

(30) Foreign Application Priority Data
Jun. 30, 2011 (KR) .................. 10-2011-0064652

(51) Int. Cl.
*A61H 15/02* (2006.01)
*A61F 7/00* (2006.01)
(Continued)

(52) U.S. Cl.
CPC ............. *A61F 7/007* (2013.01); *A61H 15/00* (2013.01); *A61F 7/00* (2013.01);
(Continued)

(58) Field of Classification Search
CPC ................................ A47C 21/048; A61F 7/00
See application file for complete search history.

(56) References Cited

U.S. PATENT DOCUMENTS

| 815,077 A | * | 3/1906 | Dougherty | ............. A47C 19/04 5/183 |
| 1,368,510 A | * | 2/1921 | Kreuzkamp | ........... A47C 17/32 5/132 |

(Continued)

FOREIGN PATENT DOCUMENTS

| CN | 87208159 U | 10/1988 |
| CN | 2621031 Y | 6/2004 |

(Continued)

OTHER PUBLICATIONS

International Search Report issued in PCT/KR2012/004609, dated Dec. 17, 2012.

*Primary Examiner* — Long V Le
*Assistant Examiner* — Luther Behringer
(74) *Attorney, Agent, or Firm* — Riverside Law LLP

(57) ABSTRACT

The present invention relates to a sliding-type apparatus for thermo-therapeutic treatment comprising: a body (1100) on which a thermo-therapeutic treatment device (1010) is arranged; a cover (1250) which is slid, and covers said thermo-therapeutic treatment device (1010); and guide grooves which are formed to slide on said body (1100). According to the present invention, if the apparatus for thermo-therapeutic treatment is not used, a lower bed member is slid such that the lower bed member can be overlapped with the body whereby a space can be easily utilized, and if the apparatus for thermo-therapeutic treatment is used, the lower bed member is easily unfolded in a sliding manner.

6 Claims, 11 Drawing Sheets

(51) Int. Cl.
*A61N 1/40* (2006.01)
*A61H 15/00* (2006.01)

(52) U.S. Cl.
CPC .............. *A61F 2007/0071* (2013.01); *A61F 2007/0095* (2013.01); *A61G 2210/90* (2013.01); *A61H 2015/005* (2013.01); *A61H 2201/0142* (2013.01); *A61H 2201/0161* (2013.01); *A61H 2201/0207* (2013.01); *A61H 2201/0228* (2013.01); *A61H 2201/1669* (2013.01); *A61H 2205/081* (2013.01); *A61H 2230/505* (2013.01); *A61N 1/403* (2013.01)

(56) References Cited

U.S. PATENT DOCUMENTS

| | | | | |
|---|---|---|---|---|
| 1,530,420 | A | * | 3/1925 | Schmitt ............... A47C 17/13 297/107 |
| 1,536,888 | A | * | 5/1925 | Kwiatkowski ........ A47C 17/32 5/18.1 |
| 3,621,192 | A | * | 11/1971 | Pohler ................... A47C 7/748 219/217 |
| 4,738,495 | A | * | 4/1988 | Mitts .................... A47B 49/006 108/140 |
| 6,871,367 | B1 | * | 3/2005 | Beckles ............... A61G 7/0005 4/547 |
| 7,645,249 | B2 | * | 1/2010 | Kim ...................... A61H 15/00 601/1 |
| 2002/0058973 | A1 | | 5/2002 | Lee |
| 2004/0015217 | A1 | | 1/2004 | Lofgren |
| 2006/0020311 | A1 | | 1/2006 | Ellis et al. |
| 2007/0239237 | A1 | | 10/2007 | Choi et al. |
| 2010/0137704 | A1 | | 6/2010 | Vij et al. |

FOREIGN PATENT DOCUMENTS

| | | |
|---|---|---|
| CN | 2410752 Y | 1/2005 |
| CN | 2673206 Y | 1/2005 |
| CN | 1579576 A | 2/2005 |
| CN | 2720667 Y | 8/2005 |
| CN | 101099702 A | 1/2008 |
| CN | 201561474 U | 8/2010 |
| JP | U11987015257 | 1/1987 |
| JP | 2001517491 A | 10/2001 |
| KR | 20020059306 A | 7/2002 |
| KR | 20-0317373 | 6/2003 |
| KR | 20-0339493 | 1/2004 |
| KR | 10-0482247 | 4/2005 |
| KR | 20-0406883 | 1/2006 |
| KR | 20100003751 U | 4/2010 |
| KR | 20110000909 U | 1/2011 |

* cited by examiner

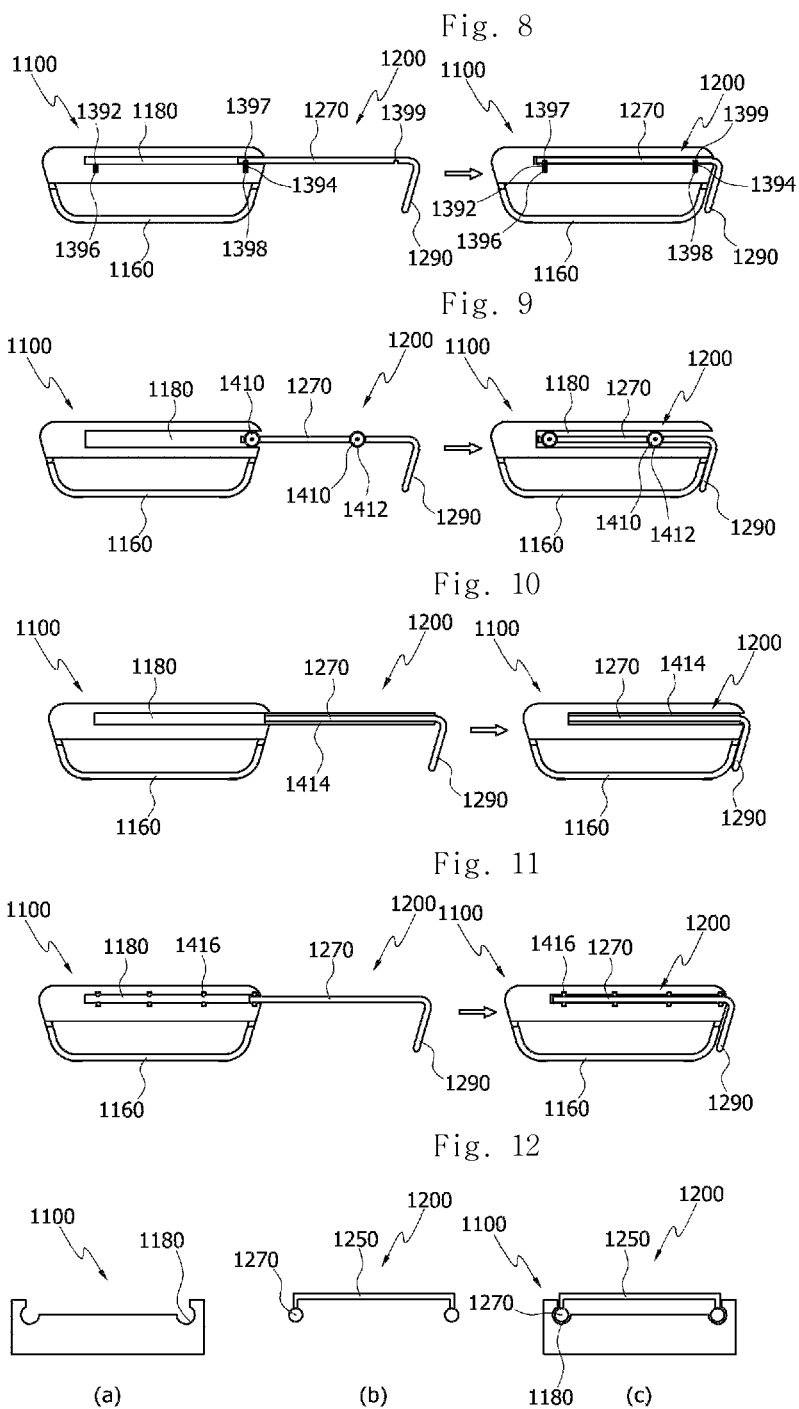

Fig. 20
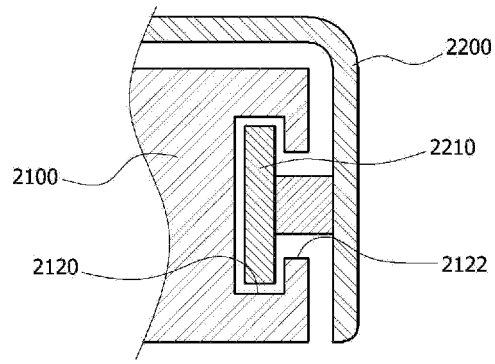
(a)
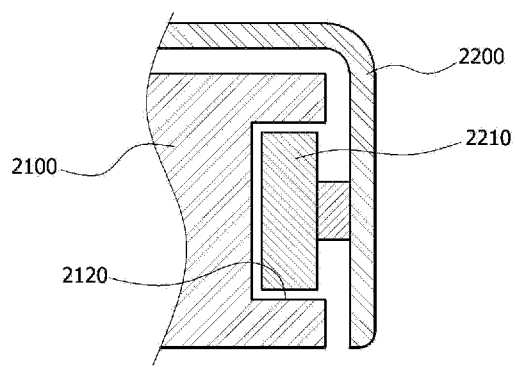
(b)
Fig. 21
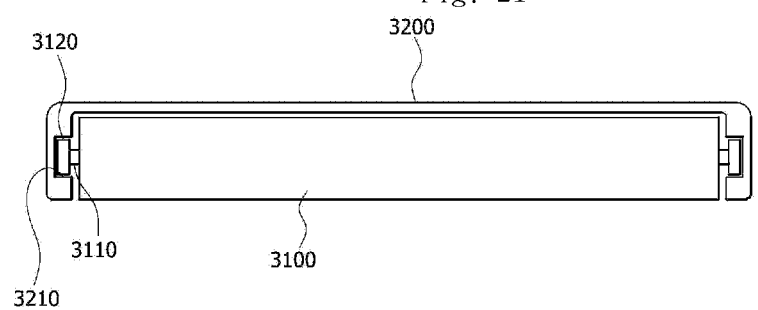

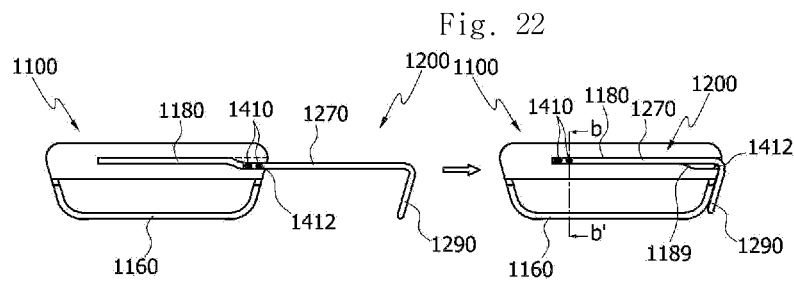
Fig. 22
(a)
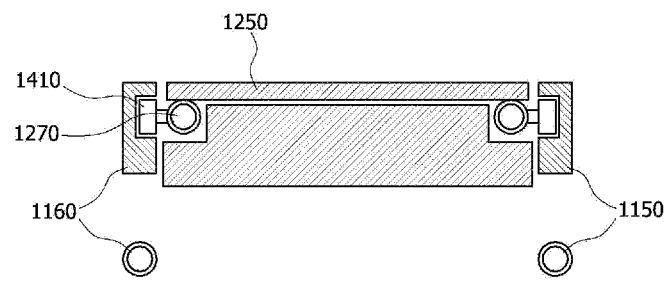
(b)
Fig. 23
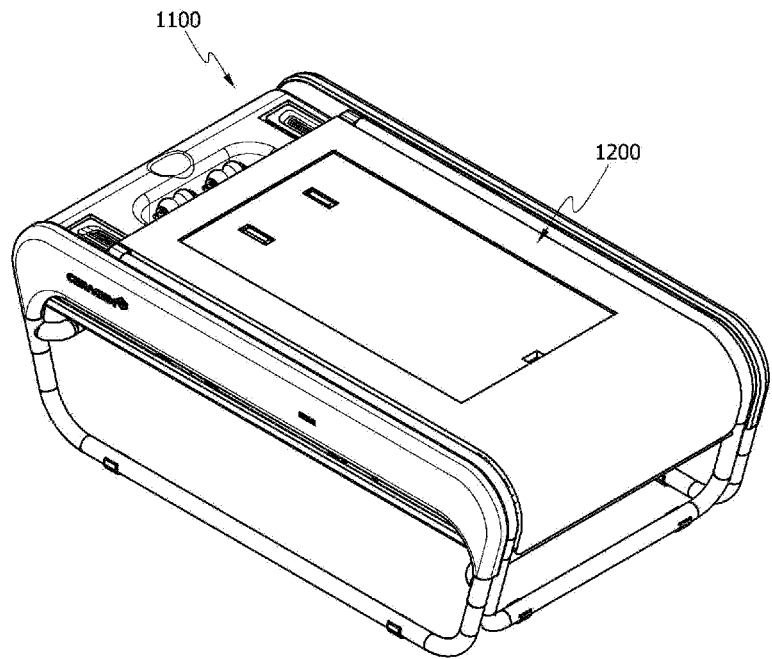

Fig. 26
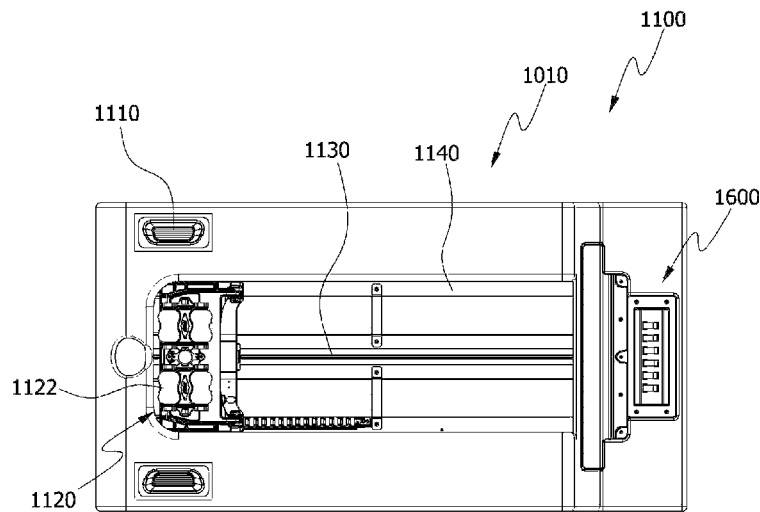
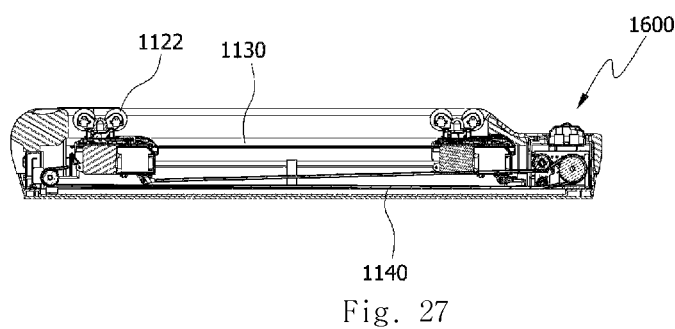
Fig. 27
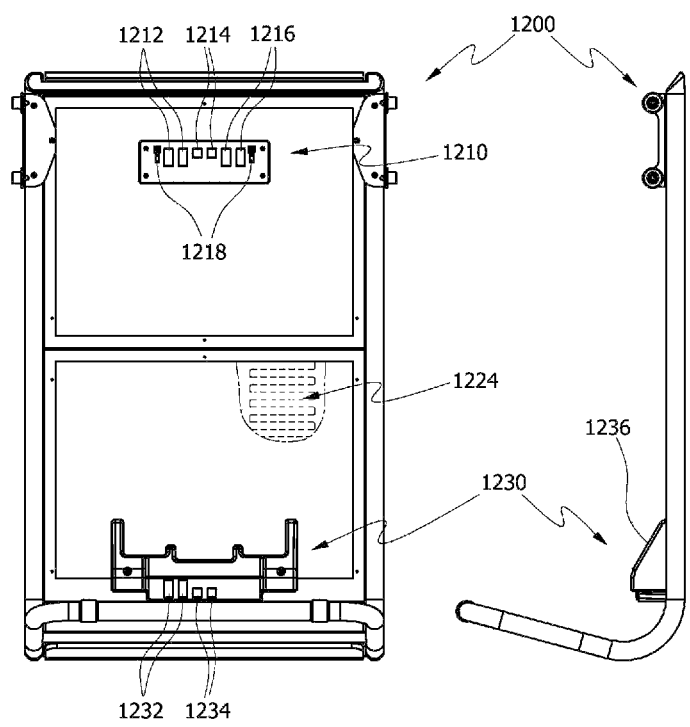
(a)  (b)

SLIDING-TYPE APPARATUS FOR THERMOTHERAPEUTIC TREATMENT

CROSS-REFERENCE TO RELATED APPLICATIONS

This application is the U.S. national phase application filed under 35 U.S.C. §371 claiming benefit to International Patent Application No. PCT/KR2012/004609, filed on Jun. 11, 2012, which is entitled to priority under 35 U.S.C. §119(a)-(d) to Korea application no. 10-2011-0064652, filed Jun. 30, 2011, each of which application is hereby incorporated herein by reference in its entirety.

TECHNICAL FIELD

The present invention relates to a sliding-type apparatus for thermo-therapeutic treatment.

BACKGROUND ART

Generally, in order to ease acute or chronic pain occurring in muscles and nervous tissues of a spine region due to incorrect posture and habituation of such incorrect posture, improve blood circulation in one's body, or relieve sudden muscle strain, a thermo-therapeutic treatment apparatus which moves along body parts and improves blood circulation through stimulation using thermo-therapeutic treatment is used widely.

However, since a conventional thermo-therapeutic treatment apparatus is in the form of a general bed which cannot be folded, it takes up much space even when not used.

DISCLOSURE

Technical Problem

The present invention is directed to providing a sliding-type apparatus for thermo-therapeutic treatment, which can reduce an occupied space when it is not used.

Also, the present invention is directed to providing a sliding-type apparatus for thermo-therapeutic treatment, which can reduce an occupied space and in which structural deformation can be simply achieved.

Technical Solution

One aspect of the present invention provides a sliding-type apparatus for thermo-therapeutic treatment, including a body 1100 in which a thermo-therapeutic treatment device 1010 is disposed, a cover 1250 which is slid to cover the thermo-therapeutic treatment device 1010, and a guide groove for sliding, which is formed in the body 1100.

Another aspect of the present invention provides a sliding-type apparatus for thermo-therapeutic treatment, including a body 1100 in which a thermo-therapeutic treatment device 1010 is disposed, a cover 1250 which is slid to cover the thermo-therapeutic treatment device 1010, and a guide groove for sliding, which is formed in the cover 1250.

The cover 1250 may include a frame which is moved along the guide groove, and the body 1100 may include a frame which is moved along the guide groove.

The body 1100 may have a guide protrusion, and the guide protrusion may have a roller, and the cover 1250 may have a heating element, and the cover 1250 may have a roller.

The guide groove may be formed at one of the frame and upper, side and lower portions of the thermo-therapeutic treatment device, and a fixing portion may be formed at the guide groove or the frame.

The fixing portion may be one of a stepped portion, a protrusion, a concave portion and a solenoid member, and a bearing may be provided at the guide groove or the frame, and an electrode terminal may be formed at a lower end of the thermo-therapeutic treatment device, and a terminal part connected with the electrode terminal may be formed at upper and lower ends of the cover.

The heating element of the cover may be operated through the terminal even when the cover is closed.

Still another aspect of the present invention provides a sliding-type apparatus for thermo-therapeutic treatment, including a body 1100 in which a thermo-therapeutic treatment device 1010 is disposed, a lower bed member 1200 which is slid on the body 1100 to be unfolded or overlapped so that a length thereof is changed, and a body terminal part 1600 which is formed at a lower portion of the body 1100.

The body terminal part 1600 may include a body power terminal 1602, a body temperature sensor terminal 1604 and a body opening sensor terminal 1606, and the lower bed member may include a lower bed upper terminal part 1210 which is in contact with the body terminal part when the lower bed member is completely unfolded from the body.

The lower bed member may include a lower bed lower terminal part 1230 which is in contact with the body terminal part 1600 when the lower bed member 1200 is completely overlapped on the body 1100, and a limit switch 1218 may be provided at both sides of the lower bed upper terminal part 1210 to cut off power supplied to the lower bed lower terminal part 1230 when the body terminal part 1600 is in contact with the lower bed upper terminal part 1210.

The lower bed upper terminal part 1210 may include an upper power terminal 1212, an upper temperature sensor terminal 1214 and a complete opening sensor terminal 1216, and the body terminal part may include a terminal housing 1610 buried in the body 1100, a terminal cover 1620 covering the terminal housing 1610, a cover elastic member 1630 installed in the terminal housing 1610 to elastically support the terminal cover 1620, and terminals protruding to an outside through terminal holes 1624 formed in an upper surface of the terminal cover 1620.

Advantageous Effects

According to the present invention as described above, when the apparatus for thermo-therapeutic treatment is not used, the lower bed member is slid to be overlapped on the body, thereby enhancing space occupancy, and when the apparatus for thermo-therapeutic treatment is used, the lower bed member can be easily unfolded in a sliding manner.

DESCRIPTION OF DRAWINGS

FIG. 8 is a front view illustrating a state in which an automatic stopper structure is formed.

FIG. 9 is a schematic view illustrating that a wheel is installed at a rod frame.

FIG. 10 is a schematic view illustrating that a cloth member having a desired thickness is formed around the rod frame.

FIG. 11 is a schematic view illustrating that multiple bearing structures are formed in a guide groove.

FIG. 12 is a schematic view illustrating that the guide groove of a body is formed at upper portions of both edges of the body.

FIG. 20 is an enlarged cross-sectional view illustrating an A portion of FIG. 19.

FIG. 21 is a cross-sectional view illustrating that an installation position of a roller is changed in FIG. 19.

FIG. 22 is a cross-sectional view illustrating an installation structure of an inner roller of a bed in FIG. 1.

FIG. 23 is a perspective view illustrating that a lower bed member is overlapped on the body.

FIG. 26 is a plane view and a side cross-sectional view of FIG. 25.

FIG. 27 is a bottom view and a side view of the lower bed member of FIG. 24.

MODES OF THE INVENTION

Figure 1:
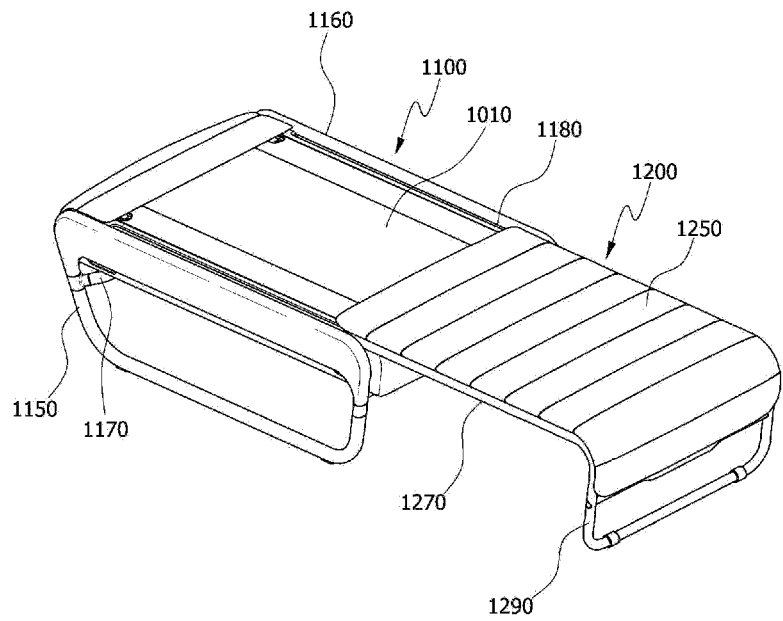
FIG. 1 is a perspective view illustrating a state in which an apparatus for thermo-therapeutic treatment is unfolded according to the present invention.

Hereinafter, preferred embodiments of the present invention will be described in detail with reference to the accompanying drawings. It should be understood that the same reference numerals are given to the same or corresponding parts, even though they are illustrated in different drawings.

Further, in the description of the embodiments of the present invention, if it is considered that the specific description of the related and noticed functions or structures may obscure the comprehension of the present invention, the description thereof will not be omitted.

Figure 2:
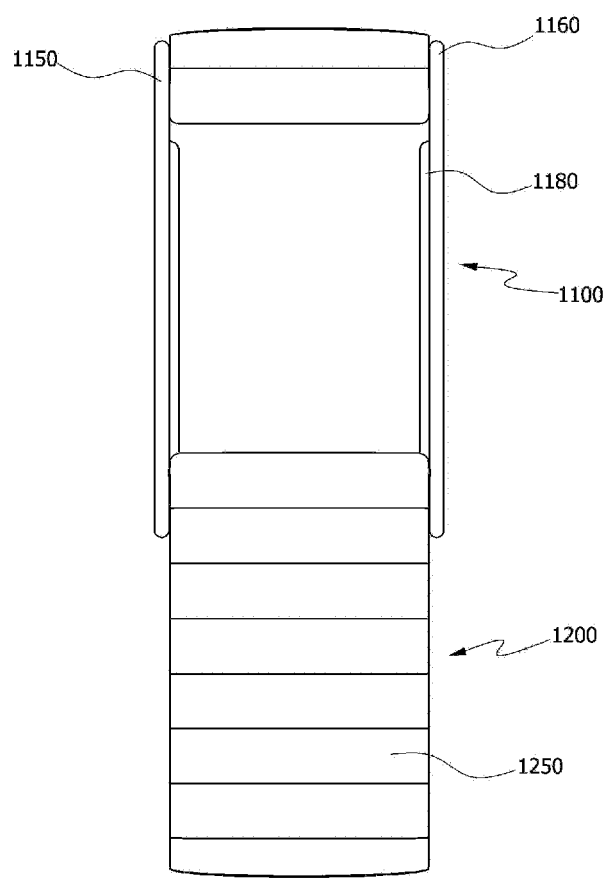
FIG. 2 is a schematic view schematically illustrating only a sliding structure in the apparatus for thermo-therapeutic treatment of FIG. 1.

FIG. 1 is a perspective view illustrating a state in which an apparatus for thermo-therapeutic treatment is unfolded according to a first embodiment of the present invention, and FIG. 2 is a schematic view schematically illustrating only a sliding structure in the apparatus for thermo-therapeutic treatment of FIG. 1.

As illustrated in FIG. 1, an apparatus for thermo-therapeutic treatment according to an embodiment of the present invention includes a body 1100 in which a thermo-therapeutic treatment device 1010 is disposed; and a lower bed member 1200 which is slid on the body 1100 to be unfolded or overlapped.

The body 110 includes the thermo-therapeutic treatment device 1010 and frames 1150 and 1160 which support the thermo-therapeutic treatment device 1010. Further, a guide groove 1180 is formed in a length direction between the thermo-therapeutic treatment device and the frame.

The thermo-therapeutic treatment device includes a thermo-therapeutic treatment mat having a hollow portion formed in a major axial direction (the above-mentioned length direction), a thermo-therapeutic treatment unit which is moved along the hollow portion in the thermo-therapeutic treatment mat, and moving means for moving the thermo-therapeutic treatment unit in the major axial direction. Therefore, while a user lies down on the apparatus for thermo-therapeutic treatment, thermo-therapeutic massage of a spine region is performed.

The frame 1150 and 1160 includes a left frame 1150, a right frame 1160, and a central connection frame 1170 connecting the left and right frames 1150 and 1160. At least one or more of the central connection frame 1170 is provided so as to support a lower portion of the thermo-therapeutic treatment device 1010.

As illustrated in drawings, the left and right frames have a roughly rectangular band shape. The left and right frames include a side frame which corresponds to a side surface of the thermo-therapeutic treatment device, a bottom frame which is supported on a bottom surface, and a connection frame which connects the side frame and the bottom frame. At this time, the frames may be manufactured in a single body, or may be manufactured in separate parts and assembled later.

Preferably, the side frame is in the form of a plate, and the bottom and connection frames are in the form of a rod.

Preferably, the side frame protrudes more than an upper surface of the thermo-therapeutic treatment device. Therefore, when the lower bed member is unfolded and a user receives the thermo-therapeutic treatment, the user is prevented from falling down through the side by the side frame. Further, when the lower bed member is overlapped on the thermo-therapeutic treatment device, a height of the side frame may be maintained to be the same as that of the lower bed member within an error range (±5%). Therefore, the apparatus for thermo-therapeutic treatment may be used as a thermo-therapeutic sofa or chair.

Here, the above-mentioned configuration may be achieved by forming the height of the side frame to be higher than that of the thermo-therapeutic treatment device, or controlling only the protruding height of the side frame.

Assuming that the height of the lower bed member is 100%, the height of the side frame which protrudes from the upper surface of the thermo-therapeutic treatment device is preferably 80 to 120%. This is due to the fact that the protruding height of the side frame may be varied according to the height of the lower bed member and may also be varied according to a height of the guide groove along which the lower bed member is slid.

The lower bed member may be slid along the guide groove of the embodiment. As illustrated in drawings, the guide groove is defined in a space between the frame and the thermo-therapeutic treatment device. In other words, one guide groove is provided between the left frame and the thermo-therapeutic treatment device, and the other guide groove is provided between the right frame and the thermo-therapeutic treatment device.

The guide groove may be formed to be long in the major axial direction in each of opposed surfaces of the frame and the thermo-therapeutic treatment device. Of course, the present invention is not limited to this. The guide groove may be formed in an inner surface of the frame opposed to the thermo-therapeutic treatment device, or in an outer surface of the thermo-therapeutic treatment device opposed to the frame. That is, the guide groove may be formed in an outer surface of the thermo-therapeutic treatment mat of the thermo-therapeutic treatment device.

The lower bed member 1200 includes a rod frame 1270 which is moved along the guide groove 1180, and an upper cover 1250 which is provided between the rod frames.

Therefore, as the rod frame 1270 is moved (or slid) forward and backward along the guide groove 1180, the lower bed member 1200 is overlapped on the body 1100, i.e., the thermo-therapeutic treatment device, or unfolded from the body 1100 to an outside.

The upper cover 1250 functions to cover and protects an upper portion of the thermo-therapeutic treatment device 1010 when the lower bed member 1200 is overlapped on the body 1100.

The upper cover 1250 includes a cover portion which is formed of cloth, leather or artificial leather, and heating means which is disposed in the cover portion. The cover portion may be formed of various other materials. The heating means is disposed at a front side of the cover portion to heat the upper cover to a desired temperature. In this embodiment, a plane heating element may be used as the heating means. Of course, the present invention is not limited to this, and various heating elements such as heat rays may be used. Here, when the plane heating element or heat rays are used, plate type members may be inserted into the upper cover in order to reduce fire risk.

When a user unfolds the lower bed member and receives thermo-therapeutic treatment of the user's spine region thereon, the user's lower body is warmed by the heating means, and thus fatigue is reduced. Further, in this embodiment, the heating means may be operated even when the upper cover overlaps the thermo-therapeutic treatment device. Thus, when the thermo-therapeutic treatment mat is used as a sofa or chair, it is possible to provide warmth to the user.

As described above, the thermo-therapeutic treatment device is provided with the thermo-therapeutic treatment mat having the hollow portion. Even though the protecting cover is disposed at an upper side of the thermo-therapeutic treatment mat, there is a disadvantage in that the apparatus for thermo-therapeutic treatment may not be used for other purposes due to the hollow portion.

In this embodiment, when the apparatus for thermo-therapeutic treatment is not used, the upper cover 1250 covers the upper side of the thermo-therapeutic treatment device 1010 so that the hollow portion is not exposed, and thus the apparatus for thermo-therapeutic treatment may be used as the thermo-therapeutic sofa or chair.

Rear ends of both rod frames 1270 of the lower bed member 1200 are bent and extend downward and then are combined with each other on the ground. That is, the rod frame includes two groove frames which correspond to the guide grooves, a bottom frame which is settled on a bottom surface when the lower bed member is unfolded, and a connection frame which connects between the two groove frames and the bottom frame. Further, if necessary, a protection frame connecting between the two groove frames may be provided between the groove frames in order to protect the upper cover and also facilitate assembling.

Therefore, a rear side of the lower bed member 1200 is supported by rear ends 1290 of both rod frames 1270.

Meanwhile, the lower bed member may have an automatic/semi-automatic structure or a manual structure. That is, the lower bed member may be directly slid by a user, or may be slid automatically and semi-automatically.

Hereinafter, variously modified automatic/semi-automatic sliding structures will be described.

For convenience of understanding, if necessary, only the rod frames 1270 are illustrated in drawings, when illustrating the lower bed member 1200. Further, in the drawings, the guide groove is formed in a frame area, but the present invention is not limited to this. As described above, the guide groove may be formed in the thermo-therapeutic treatment mat, or in both of the frame and the thermo-therapeutic treatment mat.

Figure 3:
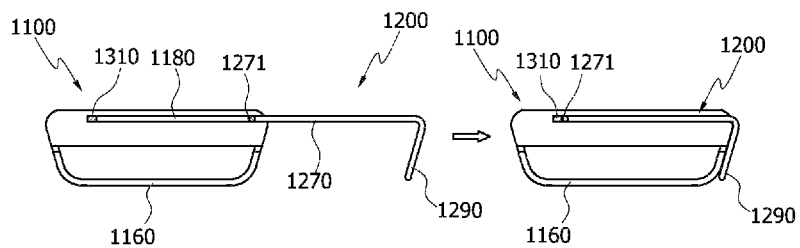
FIG. 3 is a front view of an automatic sliding structure using an electromagnet.

An automatic sliding structure according to a first modified embodiment uses an electromagnet, and FIG. 3 is a front view of the automatic sliding structure using the electromagnet. The electromagnet 1310 is installed at one side of the guide groove 1180 of the body 1100 so that the rod frame 1270 of the lower bed member 1200 is attracted by the electromagnet 1310 when electric power is supplied to the electromagnet 1310.

In this case, an iron-containing material which is easily attracted by a magnet is preferably applied to a distal end 1271 of the rod frame 1270 so that the electromagnet 1310 can function effectively. Of course, a magnet or another electromagnet which has opposite polarity to that of the electromagnet 1310 may be disposed at the distal end of the rod frame.

Figure 4:
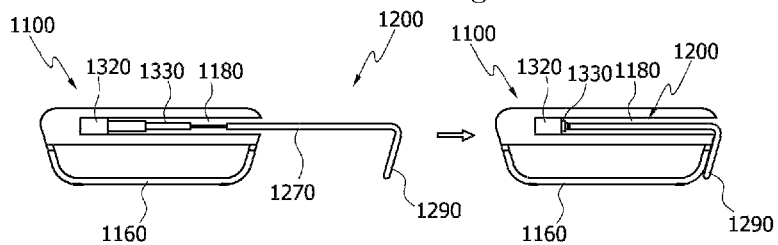
FIG. 4 is a front view of an automatic sliding structure in which a cylinder structure is applied.

Another automatic sliding structure according to a second modified embodiment uses a cylinder structure, and FIG. 4 is a front view of the automatic sliding structure in which the cylinder structure is applied. A cylinder 1320 and a piston 1330 are provided at one side of the guide groove 1180 of the body 1100 so that the piston 1330 expands from and contracts into the cylinder 1320 in order to push and pull the distal end 1271 of the rod frame 1270.

At this time, the piston 1330 is in the form of multiple cylinders which gradually become smaller. A central one of the multiple cylinders has a rod shape, and a distal end of the rod is connected to the distal end 1271 of the rod frame 1270. That is, the distal end 1271 of the rod frame 1270 may be connected with the smallest cylinder, i.e., an endmost cylinder. Therefore, when the cylinder is used, the guide groove may have a length which is longer by a length of the piston portion. Further, this modified embodiment is not limited to this, and the piston 1330 may be inserted into and operated in the rod frame 1270. To this end, a part of a piston area other than the smallest piston area may be cut away, and thus the length of the guide groove is prevented from increasing.

When the lower bed member 1200 is slid to be separated from the body 1100, a fluid is introduced into the cylinder 1320 so that the piston 1330 is expanded.

When the lower bed member 1200 is coupled with the body 1100, fluid pressure in the cylinder 1320 is reduced to come in contact with the piston 1330.

Figure 5:
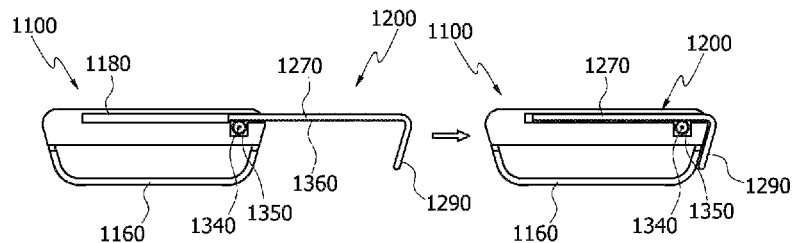
FIG. 5 is a front view of an automatic sliding structure in which a gear structure is applied.

An automatic sliding structure according to a third modified embodiment uses a gear structure, and FIG. 5 is a front view of the automatic sliding structure in which the gear structure is applied. The automatic sliding structure of the third modified embodiment includes a rack gear 1350 which is provided at the other side of the guide groove 1180 and driven by a motor 1340, and a rod frame 1270 which has a pinion gear part 1360 engaged with the rack gear 1350.

If the motor 1340 is rotated in a clockwise direction, the lower bed member 1200 is moved from the body 1100 to an outside, and if the motor 1340 is rotated in a counter-clockwise direction, the lower bed member 1200 is moved to be overlapped on the body 1100.

Figure 6:
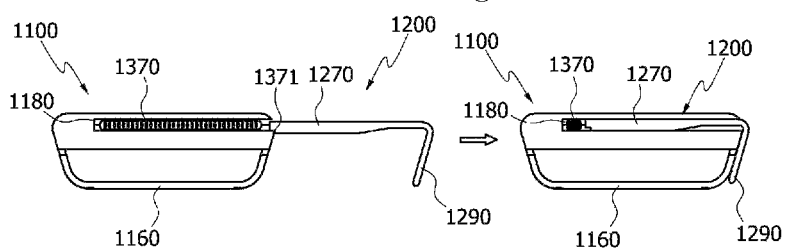
FIG. 6 is a front view of an automatic sliding structure in which a spring structure is applied.

An automatic sliding structure according to a fourth modified embodiment uses a spring structure, and FIG. 6 is a front view of the automatic sliding structure in which the spring structure is applied. In the automatic sliding structure according to the fourth modified embodiment, one end of a spring 1370 is fixed to one side of the guide groove 1180 of the body 1100, and the other end thereof is fixed to one side of the rod frame 1270.

A lower stepped portion 1371 is formed at one side of the rod frame 1270, and while the lower bed member 1200 is sufficiently moved from a center portion of the body 1100 to one side thereof, the lower stepped portion 1371 is caught at a lower portion of the guide groove 1180, and thus action of the spring 1370 is stopped.

If the lower stepped portion 1371 is lifted up, the lower bed member 1200 is moved to be overlapped on the body 1100 by the action of the spring 1370. In this modified embodiment, the guide groove 1180 preferably has a length which is increased by a length of the spring 1370.

At this time, the lower stepped portion may also be applied to a manual sliding structure as well as the automatic/semi-automatic structure.

As described above, when the automatic/semi-automatic structure is used, a separate controlling part may be further included in order to allow such driving, even though not illustrated or described in detail.

Also, combinations of the above-mentioned modified embodiments may be applied to the embodiment.

Also, a part of a technique used in one of the modified embodiments may be applied to other modified embodiments.

Meanwhile, the first embodiment may have a stopper structure so that the lower bed member 1200 is not slid while being located at one side or the other side of the guide groove 1180 of the body 1180.

Figure 7:
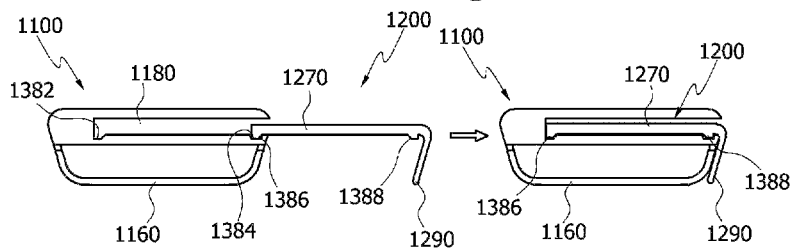
FIG. 7 is a front view illustrating a state in which a manual stopper structure is formed.

FIG. 7 is a front view illustrating a state in which a manual stopper structure is formed.

As illustrated in FIG. 7, one settling concave portion 1382 is downwardly formed at one side of the guide groove 1180 of the body 1100, and the other settling concave portion 1384 is downwardly formed at the other side of the guide groove 1180.

Opposite sides of the one settling concave portion 1382 and the other settling concave portion 1384 are inclined to each other. One lower protrusion 1386 is formed at one side of the rod frame 1270, and the other lower protrusion 1388 is formed at the other side thereof. The one lower protrusion 1386 is inserted into the one settling concave portion 1382 or the other settling concave portion 1384, and the other protrusion 1388 is inserted into the other settling concave portion 1384.

That is, if the rod frame 1270 is moved to an inner side of the guide groove 1180 so that the apparatus for thermo-therapeutic treatment is folded, the one lower protrusion 1386 of the rod frame 1270 is inserted (settled) into the one settling concave portion 1382, and the other protrusion 1388 is inserted (settled) into the other settling concave portion 1384.

If the rod frame 1270 is moved to an outer side of the guide groove 1180 so that the apparatus for thermo-therapeutic treatment is unfolded, only the one lower protrusion 1386 is inserted (settled) into the other settling concave portion 1384.

According to this embodiment, the rod frame 1270 may be stably settled in the guide groove 1180 using the one settling concave portion 1382 and the other settling concave portion 1384.

In other words, the lower bed member is prevented from folding and unfolding without the user's intent. Further, since the protrusion is inserted into the concave portion, a user can confirm states in which the apparatus is folded and unfolded through a feeling or a sound.

FIG. 8 is a front view illustrating a state in which an automatic stopper structure is formed.

In this embodiment, as illustrated in FIG. 8, lifting members 1392 and 1394 and solenoid valves 1396 and 1398 which move the lifting members 1392 and 1394 up and down are disposed at lower sides of one end and the other end of the guide groove 1180, and insertion grooves 1397 and 1399 are formed in the one end and the other end of the guide groove 1180.

If the insertion grooves 1397 and 1399 are located over the lifting members 1392 and 1394, the solenoid valves 1396 and 1398 are automatically operated by a controller or a predetermined control circuit so that the lifting members 1392 and 1394 are inserted into the insertion grooves 1397 and 1399.

When the lower bed member 1200 is unfolded, one solenoid valve 1396 is not operated, one lifting member 1392 is located at the lower side of the guide groove 1180, and the other solenoid valve 1398 is operated so that the other lifting member 1392 is lifted up and inserted into the one insertion groove 1397.

When the lower bed member 1200 is moved so as to be overlapped on the thermo-therapeutic treatment device, the operation of the other solenoid valve 1398 is stopped by the controller, the other lifting member 1394 is lowered, and the lower bed member 1200 is moved and overlapped on the body 1100.

Also, if the lower bed member 1200 is completely in contact with a predetermined position of the body 1100, the one solenoid valve 1396 and the other solenoid valve 1398 are both operated, and the one lifting member 1392 and the other lifting member 1394 are respectively inserted into the one insertion groove 1397 and the other insertion groove 1399.

Therefore, according to this embodiment, when the lower bed member 1200 is unfolded from the body 1100 or overlapped on the body 1100, the lower bed member 1200 may be automatically stopped and fixed at a desired position.

Meanwhile, in order to minimize noise and vibration generated by the rod frame 1270 moved in the guide groove 1180, the embodiment has the following configuration:

FIG. 9 is a schematic view illustrating that a wheel is installed at the rod frame, FIG. 10 is a schematic view illustrating that a cloth member having a desired thickness is formed around the rod frame, and FIG. 11 is a schematic view illustrating that multiple bearing structures are formed in the guide groove.

In this embodiment, as illustrated in FIG. 9, a wheel 1410 is installed at the rod frame 1270 so as to be moved along the guide groove 1180. A urethane member 1412 is applied on an outer circumferential surface of the wheel 1410 in order to absorb the noise and vibration.

Of course, various materials other than the urethane member 1412 may be applied, and if necessary, the urethane member may not be used.

Here, the wheel may be installed at an inner surface and/or outer surface of the rod frame 1270. In this case, the wheel is inserted into the guide groove 1180, and a part or all of the rod frame 1270 may protrude to an outside of the guide groove. Of course, the wheel and the rod frame may both be inserted into the guide groove. Herein, when only the wheel is inserted into the guide groove, the wheel may have a smaller size than the rod frame. Further, the wheel may be installed at a lower portion of the rod frame so that a part of the wheel is inserted into the rod frame. In this case, the lower portion of the rod frame may have an opened groove through which the wheel is exposed. Of course, the wheel may be disposed at other portions (an upper portion and both side portions) of the rod frame. The present invention is not limited to this, and the wheel may be disposed in the guide groove along which the rod frame is moved.

Moreover, the drawings illustrate that the wheel may be disposed at all parts of the rod frame. However, the present invention is not limited to this, and the wheel may be disposed at only a front end of the rod frame when the front end of the rod frame is in contact with the entire surface of the guide groove while being moved. Further, when a user manually slides the lower bed member, the user picks up the other portion (i.e., the opposite portion to the front end) of the lower bed member and moves it. Thus, even though the wheel is not installed at all areas of the rod frame, the lower bed member may be slid smoothly.

In this embodiment, as illustrated in FIG. 10, a cloth member 1414 formed of carbon fibers which has a very soft surface and is not worn may be applied around the rod frame 1270 in order to absorb the noise and vibration generated by friction. This embodiment is not limited to this, and the cloth member 1414 may be applied in the guide groove.

Further, as illustrated in FIG. 11, multiple bearing members 1416 may be applied in the guide groove 1180 so that a surface of the rod frame 1270 moving along the guide groove 1180 is in contact with the bearing members 1416.

Due to these structures, friction between the rod frame 1270 and the guide groove 1180 may be minimized.

Meanwhile, the body and the lower bed member may be connected in various manners which will be described later. Lower drawings illustrate a schematic description in which techniques to be described below may be applied to the above-mentioned frame and thermo-therapeutic treatment mat.

Figure 13:
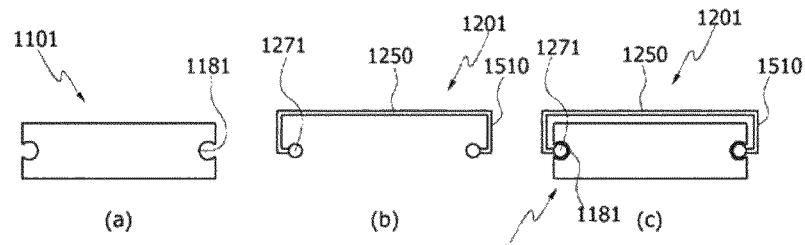
FIG. 13 is a schematic view illustrating that the guide groove of the body is formed at middle portions of both side surfaces of the body.
Figure 14:
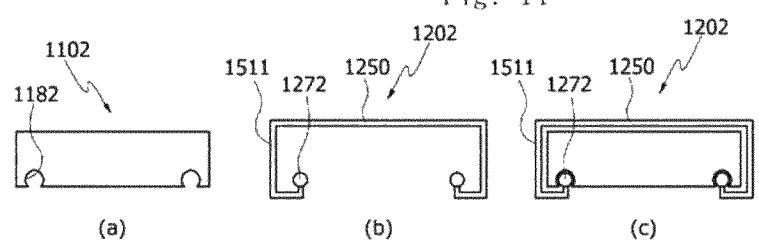
FIG. 14 is a schematic view illustrating that the guide groove of the body is formed at a lower portion of both edges of the body.

FIG. 12 is a schematic view illustrating that the guide groove of the body is formed at upper portions of both edges of the body according to a first modified embodiment, FIG. 13 is a schematic view illustrating that the guide groove of the body is formed at middle portions of both side surfaces of the body according to a second modified embodiment, and FIG. 14 is a schematic view illustrating that the guide groove of the body is formed at both edges of a lower portion of the body according to a third embodiment.

In the first modified embodiment, as illustrated in FIG. 12A, the guide groove 1180 may be formed in the upper portions of both edges of the body 1100, and as illustrated in FIG. 12B, the rod frame 1270 may be provided at both sides of the upper cover 1250 of the lower bed member 1200, and as illustrated in FIG. 12C, the rod frame 1270 of the lower bed member 1200 may be coupled into the guide groove 1180 of the body 1100. That is, the guide groove may be formed at one of the frame and the thermo-therapeutic treatment mat of the body 1100 or between the frame and the thermo-therapeutic treatment mat.

As illustrated in FIG. 13A, a guide groove 1181 may be formed in the middle portions of both side surfaces of a body 1101. Thus, a structure of the lower bed member may be changed. That is, as illustrated in FIG. 13B, a connection frame 1510 may be formed from both sides of an upper cover 1250 of a lower bed member 1201 to a position corresponding to the guide groove 1181, and a rod frame 1271 may be formed at an end of the connection frame 1510. As illustrated in FIG. 13C, the rod frame 1271 of the lower bed member 1201 may be coupled into the guide groove 1181 of the body 1101. Also, in this modified embodiment, the guide groove may be formed at one of the frame and the thermo-therapeutic treatment mat or between the frame and the thermo-therapeutic treatment mat.

For example, when the technique of the modified embodiment as illustrated in FIG. 13 is applied to the frame, in the state in which the lower bed member 1201 is overlapped on the body 1101 from an upper side, the body 1101 is not exposed, and only a half of the lower bed member 1201 is exposed, thereby improving external appearance compared with the modified embodiment in FIG. 12. Further, the body may be stably protected in the overlapped state, and when a user sits on the lower bed member, coldness from the existing frame area may be prevented.

Furthermore, as illustrated in FIG. 14A, a guide groove 1182 may be downwardly formed at the lower portions of both edges of a body 1102. As illustrated in FIG. 14B, a connection frame 1511 may be formed from both sides of an upper cover 1250 of a lower bed member 1202 to a position corresponding to the guide groove 1182, and a rod frame 1272 may be formed at an end of the connection frame 1511. As illustrated in FIG. 14C, the rod frame 1272 of the lower bed member 1202 may be coupled with the guide groove 1182 of the body 1102.

Also, in this modified embodiment, the guide groove may be formed at one of the frame and the thermo-therapeutic treatment mat of the body.

Meanwhile, as another embodiment of the present invention, a guide protrusion may be formed from the body in a length direction of the body, and a groove frame member moved along the guide protrusion may be formed at the lower bed member. That is, in the previous embodiment, the guide groove was formed in the body, and the rod frame was moved in the guide groove. However, in the following embodiment, a protrusion is formed at the body, and the guide groove is formed at the rod frame. Each technique in the following embodiments may be partially applied to other embodiments, and the technique of the first embodiment may be applied to a second embodiment, and also a technique of the second embodiment may be applied to the first embodiment.

Figure 15:
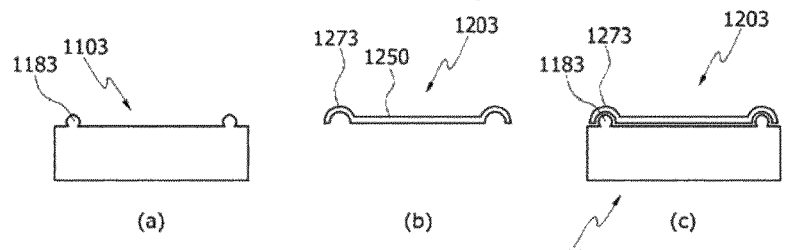
FIG. 15 is a schematic view illustrating that a guide protrusion of the body is formed at upper portions of both edges of the body.
Figure 16:
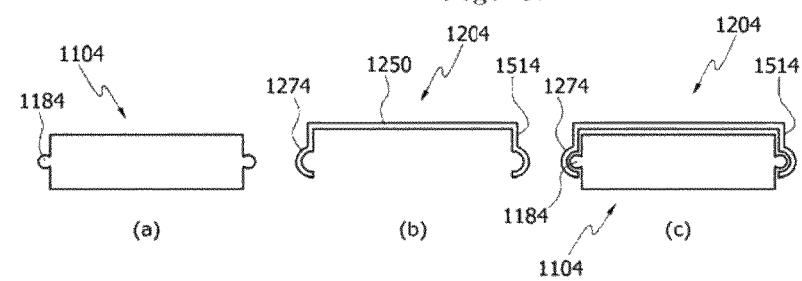
FIG. 16 is a schematic view illustrating that the guide protrusion of the body is formed at the middle portions of both side surfaces of the body.
Figure 17:
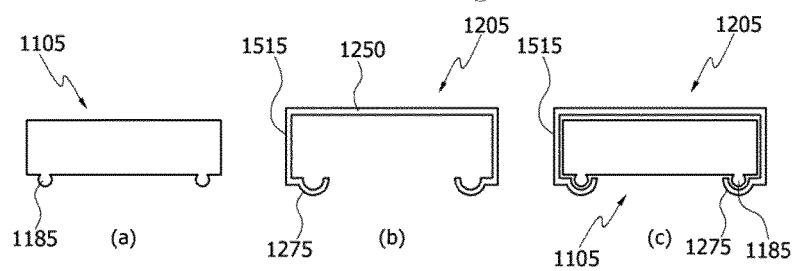
FIG. 17 is a schematic view illustrating that the guide protrusion of the body is formed at the lower portions of both sides of the body.

FIG. 15 is a schematic view illustrating that a guide protrusion of the body is formed at upper portions of both edges of the body, FIG. 16 is a schematic view illustrating that the guide protrusion of the body is formed at the middle portions of both side surfaces of the body, and FIG. 17 is a schematic view illustrating that the guide protrusion of the body is formed at the lower portions of both sides of the body.

As illustrated in FIG. 15A, a body 1103 includes a guide protrusion 1183 protruding from upper portions of both edges thereof. As illustrated in FIG. 15B, a lower bed member 1203 has a groove frame 1273 formed at both edges of an upper cover 1250. As illustrated in FIG. 15C, the guide protrusion 1183 of the body 1103 is coupled with the groove frame 1273 of the lower bed member 1203 and moved (slid) together. Here, it is preferable that the groove frame not be separated from the body until the lower bed member is completely unfolded by the protrusion and groove structure. Further, the guide protrusion may be formed at one of the frame and the thermo-therapeutic treatment mat, or between the frame and the thermo-therapeutic treatment mat. If the guide protrusion is formed between the frame and the thermo-therapeutic treatment mat (i.e., at both areas of the frame and the thermo-therapeutic treatment mat), two grooves may be formed in the groove frame. Of course, the number of groove frames may be varied according to the number of guide protrusions. The guide protrusion may be in the form of a dot, dots arranged in a line, or a line.

In the drawing illustrating the groove frame, the whole rod is curved. However, the present invention is not limited to this, and the rod frame may be partially bent or cut away.

As illustrated in FIG. 16A, the guide protrusion may be formed at middle portions of both side surfaces of a body 1104. Therefore, as illustrated in FIG. 16B, a connection frame 1514 may be formed from both side surfaces of an upper cover 1250 of a lower bed member 1204 to a position corresponding to the guide protrusion 1184, and a groove frame 1274 may be formed at an end of the connection frame 1514. As illustrated in FIG. 16C, the guide protrusion 1184 of the body 1104 is coupled with the groove frame 1274 of the lower bed member 1204 and moved together.

As illustrated in FIG. 17A, a guide protrusion may be formed at the lower portions of both edges of a body 1105. In FIG. 17B, a connection frame 1515 may be formed from both sides of an upper cover 1250 of a lower bed member 1205 to a position corresponding to the guide protrusion 1185, and a groove frame 1274 may be formed at an end of the connection frame 1515. As illustrated in FIG. 17C, the groove frame 1275 of the lower bed member 1205 may be coupled with the guide protrusion 1185 of the body 1102 and moved together.

Figure 18:
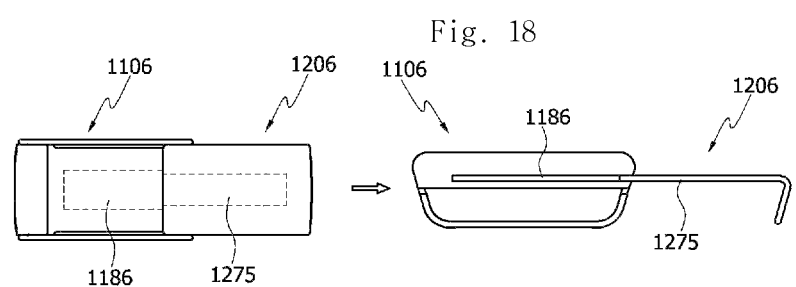
FIG. 18 is a schematic view illustrating a state in which the guide groove is formed at a central lower portion of the body.

FIG. 18 is a schematic view illustrating a state in which the guide groove is formed at a central lower portion of the body according to a third embodiment of the present invention.

In this embodiment as illustrated in FIG. 18, a guide groove is formed in the hollow portion of the thermo-therapeutic treatment mat, and a plate frame inserted into the hollow portion and the guide groove is provided at the lower bed member. Therefore, if the lower bed member is overlapped, the hollow portion of the thermo-therapeutic treatment mat is completely blocked, and thus a therapeutic treatment ceramic disposed in the hollow portion may be protected.

Of course, the present invention is not limited to this, and a plate type guide groove may be formed in an upper portion of the therapeutic treatment mat, and a plate type frame inserted into the plate type guide groove may be provided in the lower bed member.

Further, in this embodiment, the frame may not be used in the body.

Figure 19:
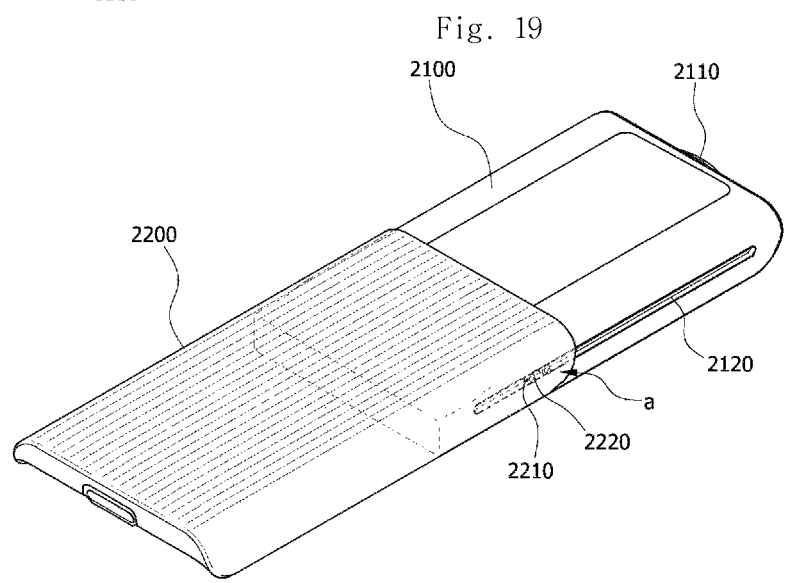
FIG. 19 is a perspective view of a sliding-type apparatus for thermo-therapeutic treatment, in which a frame structure is not provided.

FIG. 19 is a perspective view of a sliding-type apparatus for thermo-therapeutic treatment, in which a frame structure is not provided, according to a third embodiment of the present invention, and FIG. 20 is an enlarged cross-sectional view illustrating an A portion of FIG. 19A.

In this embodiment, instead of the sliding type apparatus for therapeutic treatment having the frame structure illustrated in FIGS. 1 to 18, an apparatus for thermo-therapeutic treatment in which a frame structure is not provided may be provided as illustrated in FIG. 19.

A technique in this embodiment may also be applied to the above-mentioned embodiments. Further, any duplicate description thereof will be omitted.

An apparatus for therapeutic treatment according to this embodiment includes a cover portion which covers the therapeutic treatment device.

The therapeutic treatment device includes a therapeutic treatment mat 2100 having a guide groove 2120 formed in a length direction in both side surfaces thereof, and a therapeutic treatment ceramic which moves along the hollow portion of the therapeutic treatment mat and massages a user's spine region.

The cover portion is formed to enclose upper and side surfaces of the therapeutic treatment mat 2100. The cover portion includes a roller 2210 which is moved along the guide groove 2120, and a cover 2200 having a rotational shaft 2220 of the roller 2210.

Further, a handle 2110 may be provided at an end of the apparatus for therapeutic treatment.

A user pulls the handle 2110 and unfolds the therapeutic treatment mat 2100 from the cover 2200 in a sliding manner and then receives the therapeutic treatment. After the therapeutic treatment, the user inserts the therapeutic treatment 2100 into the cover 2200 in order to reduce a whole volume thereof.

When the therapeutic treatment mat 2100 is inserted into or unfolded from the cover 2200, the roller 2210 is rotated along the guide groove 2120 in order to allow the therapeutic treatment mat 2100 to be easily inserted and unfolded.

In a method of connecting the roller 2210 with the guide groove 2120, as illustrated in FIG. 20A, a stepped groove 2122 and the guide groove 2120 having a larger diameter than the stepped groove 2122 are formed in the therapeutic treatment mat 2100, and the roller 2210 is moved in the guide groove 2120. Otherwise, as illustrated in FIG. 20B, the guide groove 2120 is formed in the therapeutic treatment mat 2100 without the stepped groove 2122, and the roller 2210 is moved in the guide groove 2120. In this case, a side area of the therapeutic treatment mat is preferably formed of a plastic or synthetic resin material. That is, it is preferable that the side area be formed of a material which can increase shock resistance and can minimize pressure and friction generated when the roller is moved.

In this embodiment, as illustrated in FIGS. 20A and 20B, the roller is disposed in the guide groove. The roller is connected to a side surface of the cover. Herein, the cover includes an upper cover body which covers an upper portion of the therapeutic treatment mat, and a side cover body which covers a side surface thereof. The roller is coupled and fixed to an inner side surface of the side cover body. Of course, like in the above-mentioned embodiments, a part of the side cover body protrudes and extends into the guide groove to be slid.

As illustrated in FIG. 20B, the guide groove may be formed so that an outer side surface thereof is opened, and as illustrated in FIG. 20A, the guide groove may be formed to have protrusions that protrude upward and downward from an opening area. At this time, the method of FIG. 20A is more firmly configured so that the roller is not separated from the guide groove, compared with that of FIG. 20B.

FIG. 21 is a cross-sectional view illustrating that an installation position of a roller is changed in FIG. 19.

In this embodiment, a guide groove 3210 is formed in both side surfaces of a cover 3200, as illustrated in FIG. 21, and a roller 3120 which is rotated about a rotational shaft 3110 is provided at both sides of a body 3100 and moved in the guide groove 3210.

FIG. 22 is a cross-sectional view illustrating an installation structure of an inner roller of a bed in FIG. 1.

FIG. 22 illustrates a structure in which a wheel 1410 is moved in only a body 1100. A portion of a guide groove 1180 in which the wheel 1410 is moved is formed in frames 1150 and 1160.

The guide groove 1180 is inclined downward at a lower portion of the body 1100 and then formed horizontally again. Since a height of a lower bed member 1200 is higher than that of the guide groove 1180, an inclined sliding surface 1189 which is the downwardly inclined portion is formed to have a height corresponding to a height difference between the guide groove 1180 and the lower bed member 1200, and thus the lower bed member 1200 is maintained in a horizontal state when completely unfolded from the body 1100.

The inclined sliding surface 1189 is formed at a lower side of the thermo-therapeutic treatment device 1010 as well as the guide groove 1180.

Figure 24:
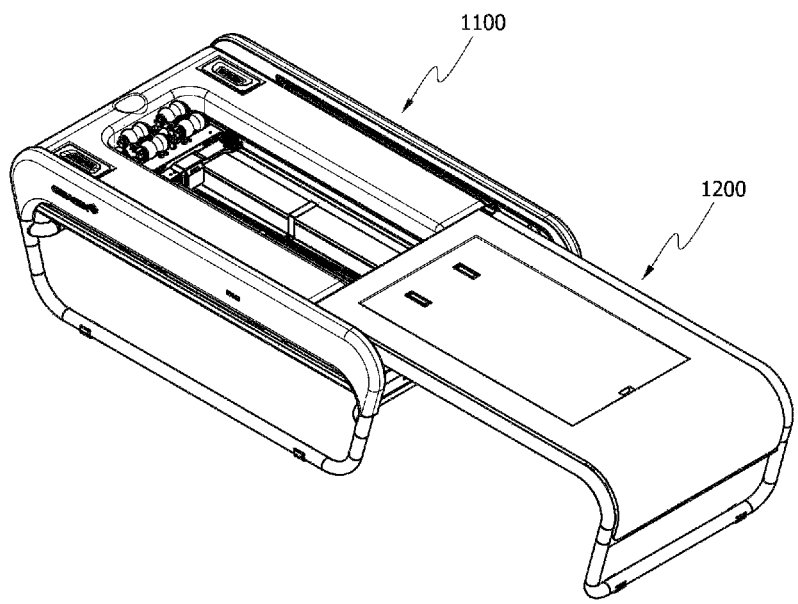
FIG. 24 is a perspective view illustrating that the lower bed member is unfolded from the body.
Figure 25:
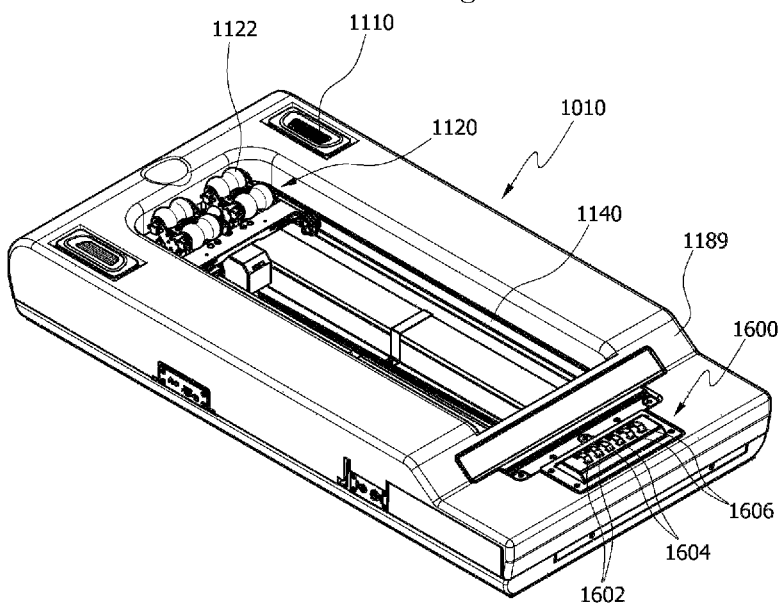
FIG. 25 is a perspective view of a thermo-therapeutic treatment device installed in the body of FIG. 24.

FIG. 23 is a perspective view illustrating that the lower bed member is overlapped on the body, FIG. 24 is a perspective view illustrating that the lower bed member is unfolded from the body, FIG. 25 is a perspective view of the thermo-therapeutic treatment device installed in the body of FIG. 24, and FIG. 26 is a plane view and a side cross-sectional view of FIG. 25.

Referring to FIGS. 23 and 24 in which an outer cover covering the body 100 and the lower bed member 1200 is omitted, FIG. 23 illustrates a state in which the lower bed member 1200 is overlapped on the body 1100 while the thermo-therapeutic treatment mat is not used, and in this state, the thermo-therapeutic treatment mat may be used as a sofa.

FIG. 24 illustrates a state in which the lower bed member 1200 is unfolded from the body 1100 while the thermo-therapeutic treatment mat is used, and in this state, a user lies on the thermo-therapeutic treatment mat and receives the thermo-therapeutic treatment.

In the thermo-therapeutic treatment device 1010 disposed in the thermo-therapeutic treatment mat, as illustrated in FIGS. 25 and 26, a ceramic installation part 1120 in which ceramics 1122 are installed treats a patient while being moved in a length direction of the thermo-therapeutic treatment mat. A moving member 1130 such as a chain, which moves the ceramic installation part 1120, is disposed at a center of the body 1100 along a length direction thereof. A guide part 1140 in the form of a guide rail, which guides the ceramic installation part 1120, is formed at lower ends of both sides of a moving passage of the ceramic installation part 1120. Here, the guide part is preferably formed at a frame of the body.

Further, an acoustic member 1110 is provided at both sides of an upper end portion of the thermo-therapeutic treatment mat spaced apart from a moving space of the ceramic installation part 1120, i.e., at both sides of a portion in which a head part of a patient is located, and thus the patient may receive music treatment as well as thermo-therapeutic treatment.

Meanwhile, a body terminal part 1600 is provided at a lower side of the thermo-therapeutic treatment mat, which is spaced part from the moving space of the ceramic installation part 1120.

The body terminal part 1600 includes a body power terminal 1602, a body temperature sensor terminal 1604 and a body opening sensor terminal 1606.

Figure 28:
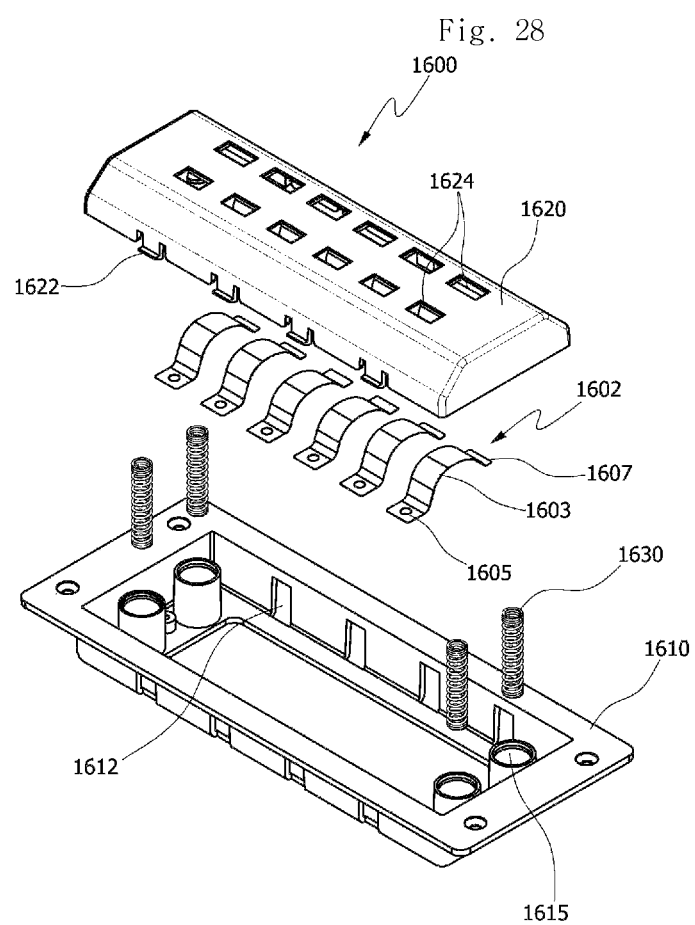
FIG. 28 is an exploded perspective view of a body terminal part.
Figure 29:
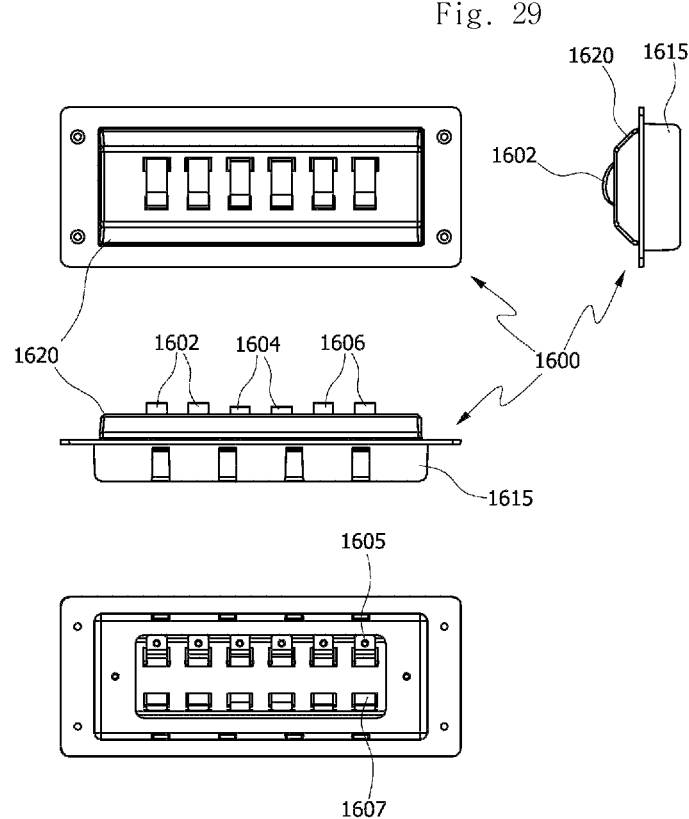
FIG. 29 is a plane view, a front view, a bottom view and a side view of the body terminal part.

FIG. 27 is a bottom view and a side view of the lower bed member of FIG. 24, FIG. 28 is an exploded perspective view of the body terminal part, and FIG. 29 is a plane view, a front view, a bottom view and a side view of the body terminal part.

The lower bed member 1200 includes a lower bed upper terminal part 1210 which is in contact with the body terminal part 1600 when the lower bed member 1200 is completely unfolded from the body 1100, and a lower bed lower terminal part 1230 which is in contact with the body terminal part 1600 when the lower bed member 1200 is completely overlapped on the body 1100.

The lower bed upper terminal part 1210 includes an upper power terminal 1212, an upper temperature sensor terminal 1214 and a complete opening sensor terminal 1216 at each position that corresponds, in turn, to the body power terminal 1602, the body temperature sensor terminal 1604 and the body opening sensor terminal 1606.

A limit switch 1218 is provided at both sides of the lower bed upper terminal part 1210 and functions to cut off power supplied to the lower bed lower terminal part 1230 when the body terminal part 1600 is in contact with the lower bed upper terminal part 1210.

In the present invention, a heating element 1224 formed of a hot wire such as a nichrome wire is built in the lower bed member 1200 in order to transfer heat to a user's leg region. Here, it is necessary to supply power to the heating element 1224 and detect and control a temperature of the heating element 1224.

A device for supplying the power to the heating element 1224 and detecting and controlling the temperature may be provided on the lower bed member 1200. However, in the present invention, a power part of the body 1100 is in charge of supplying power to the heating element 1224, and a function of detecting and controlling temperature is performed through the body 1100 and a remote controller.

If the body power terminal 1602 is in contact with the upper power terminal 1212, a current from the body 1100 is transmitted to the lower bed member 1200.

If the body temperature sensor terminal 1604 is in contact with the upper temperature sensor terminal 1214, the temperature of the heating element 1224 of the lower bed member 1200 is detected and transmitted to the control part of the body 1100.

If the body opening sensor terminal 1606 is in contact with the complete opening sensor terminal 1216, the fact that the lower bed member 1200 is unfolded from the body 1100 is transmitted to the control part of the body 1100.

The control part controls the thermo-therapeutic treatment device 1010 to be operated.

Therefore, if the body opening sensor terminal 1606 is not in contact with the complete opening sensor terminal 1216, the thermo-therapeutic treatment device 1010 is not operated by the control part, and the ceramics 1122 of the ceramic installation part 1120 are located at a lowermost area so as not to be in contact with the lower bed member 1200.

Due to the above-mentioned structure, the lower bed member 1200 is overlapped on the body when the thermo-therapeutic treatment device is not used, and thus, while the body opening sensor terminal 1606 is not in contact with the complete opening sensor terminal 1216, the ceramics 1122 of the ceramic installation part 1120 are located at the lower area.

The lower area means a lowermost area in a structure for moving the ceramics 1122 up and down.

In order to operate the apparatus for thermo-therapeutic treatment, if the lower bed member 1200 is slid to an outside of the body 1100 by a user and the lower bed upper terminal part 1210 is in contact with the body terminal part 1600, the body power terminal 1602 and the upper power terminal 1212 are connected with each other, and the power is supplied from the body 1100 to the heating element 1224 of the lower bed member 1200.

Also, the body temperature sensor terminal 1604 and the upper temperature sensor terminal 1214 are connected with each other, and the temperature of the heating element 1224 is detected and then transferred to the body 1100. The body opening sensor terminal 1606 and the complete opening sensor terminal 1216 are connected with each other, and the thermo-therapeutic treatment device 1010 is operated by the control part.

Meanwhile, if the connection between the body temperature sensor terminal 1604 and the upper temperature sensor terminal 1214 is achieved earlier than the connection between the body power terminal 1602 and the upper power terminal 1212, sparks are generated. In order to prevent the generation of sparks, the present invention has the following configuration:

Firstly, as illustrated in FIG. 27, a length of the upper power terminal 1212 is formed to be longer than that of the upper temperature sensor terminal 1214, and upper ends of the upper power terminal 1212 and the upper temperature sensor terminal 1214 are located on the same level with respect to an upper end of the lower bed member 1200, and thus a lower end of the upper power terminal 1212 is located lower than that of the upper temperature sensor terminal 1214.

Therefore, when the lower bed member 1200 is slid to the outside of the body 1100, the upper power terminal 1212 first comes in contact with the body power terminal 1602, and then the upper temperature sensor terminal 1214 comes in contact with the body temperature sensor terminal 1604.

Secondly, as shown in FIG. 29, each terminal formed in the body terminal part 1600 has a different installation height. An upper end of the body power terminal 1602 is formed to be higher than that of the body temperature sensor terminal 1604, and thus when the lower bed member 1200 is moved down along the inclined sliding surface 1189, the contact between the upper power terminal 1212 and the body power terminal 1602 is achieved earlier than that between the upper temperature sensor terminal 1214 and the body temperature sensor terminal 1604.

Thirdly, by previous programming, a contacting effect occurs after a certain time interval, preferably 5 seconds after the contact between the upper temperature sensor terminal 1214 and the body temperature sensor terminal 1604 is achieved. Therefore, even if the contact between the upper power terminal 1212 and the body power terminal 1602 and the contact between the upper temperature sensor terminal 1214 and the body temperature sensor terminal 1604 are achieved at the same time, or the contact between the upper power terminal 1212 and the body power terminal 1602 is 4 seconds later than the contact between the upper temperature sensor terminal 1214 and the body temperature sensor terminal 1604, the contacting effect between the upper power terminal 1212 and the body power terminal 1602 occurs sooner than that between the upper temperature sensor terminal 1214 and the body temperature sensor terminal 1604.

Because the above-mentioned three stabilization systems are built in the present invention, it is possible to prevent the generation of sparks.

Meanwhile, the present invention employs an elastic structure so that the terminals of the body terminal part 1600 can easily come in contact.

That is, the body terminal part 1600 includes a terminal housing 1610 buried in the body 1100, a terminal cover 1620 covering the terminal housing 1610, a cover elastic member 1630 installed in the terminal housing 1610 to elastically support the terminal cover 1620, and terminals protruding to an outside through terminal holes 1624 formed in an upper surface of the terminal cover 1620.

A cylindrical elastic member settling portion 1615 in which a lower portion of the spring-shaped cover elastic member 1630 is settled is formed in the terminal housing 1610.

The terminal cover 1620 has a cover protrusion 1622, and the terminal housing 1610 has a protrusion stopper portion 1612 which restricts a moving range of the cover protrusion 1622 to prevent the terminal cover 1620 from being separated from the terminal housing 1610.

Therefore, when the terminal cover 1620 is moved down by contact of the terminals, the terminal cover 1620 is elastically supported by the cover elastic member 1630.

Thus, according to the present invention, impact force generated when the terminals of the lower bed member 1200 moved down along the inclined sliding surface 1189 are in contact with the body terminal part 1600 is absorbed, and since the terminals of the body terminal part 1600 protrude, the contact is rapidly achieved.

As illustrated in FIG. 28, the terminal cover 1620 has a total of 12 holes 1624 in which 6 pairs of holes 1624, each pair being arranged in a width direction, are formed in a length direction.

The terminals are coupled in the terminal cover 1620 through the holes 1624. Here, one body power terminal 1602 is described as an example, and the other 5 have the same coupling structure.

The body power terminal 1602 is in the form of a thin and long plate and has a central portion 1603 curved in the form of a semicircle, one end having a fixing portion 1605, and the other end having a flat non-fixing portion 1607.

The central portion 1603 of the body power terminal 1602 is exposed to an upper side of the terminal cover 1620, the fixing portion 1605 and the non-fixing portion 1607 are inserted into two terminal holes 1624 formed in the width direction of the terminal cover 1620, the fixing portion 1605 is fixed to an inside of the terminal cover 1620 by a screw or the like, and the non-fixing portion 1607 is disposed in an unfixed state.

Therefore, when the upper power terminal 1212 is in contact with the body power terminal 1602, the central portion 1603 is contacted, and the non-fixing portion 1607 is elastically moved down with respect to the fixing portion 1605.

In the present invention, since the terminal cover 1620 is elastically moved, and the body power terminal 1602 is also elastically moved, it is doubly ensured that the contact is rapidly achieved and sufficient absorption and restoration force for impact generated when the contact is achieved are provided.

Further, the fixing portion 1605 is located lower than the non-fixing portion 1607 at a lower side of the body 1100.

This is due to the fact that, when the lower bed member 1200 is unfolded from the body 1100, the lower bed upper terminal part 1210 of the lower bed member 1200 is moved down by the inclined sliding surface 1189 and comes in contact with the body terminal part 1600, and if the lower bed member 1200 is slid to be overlapped on the body 1100, the lower bed upper terminal part 1210 of the lower bed member 1200 is moved down along the inclined sliding surface 1189 while generating friction with the body terminal part 1600, and thus if the non-fixing portion 1607 is located lower than the fixing portion 1605, the central portion 1603 is deformed in a sliding direction of the lower bed member 1200 by friction with a lower surface of the lower bed member 1200, whereby the non-fixing portion 1607 may be separated from the hole 1624 and then exposed to an upper side of the terminal cover 1620.

A length of the central portion 1603 of the body power terminal 1602 is formed to be longer than that of the central portion 1603 of the body temperature sensor terminal 1604, and the upper end of the body power terminal 1602 exposed to the upper side of the terminal cover 1620 is formed to be higher than that of the body temperature sensor terminal 1604 by increasing curvature thereof, thereby obtaining the characteristic of preventing the generation of sparks.

Meanwhile, the lower bed lower terminal part 1230 has a lower bed inclined surface 1236 corresponding to the inclined sliding surface 1189.

Also, the lower bed lower terminal part 1230 has a lower power terminal 1232 and a lower temperature sensor terminal 1234. The lower power terminal 1232 is in contact with the body power terminal 1602 when the lower bed member 1200 is overlapped on the body 1100, and the lower temperature sensor terminal 1234 is connected to the body temperature sensor terminal 1604, and thus the heating element 1224 generates heat.

Therefore, in the present invention, when the lower bed member 1200 is not unfolded, a user may use the lower bed member 1200 as a sofa. At this time, if the heating element 1224 generates heat, the lower bed member 1200 may be used as a thermo-therapeutic sofa.

The lower bed lower terminal part 1230 does not have the complete opening sensor terminal because the lower bed lower terminal part 1230 is in contact with the body terminal part 1600 only when the lower bed member 1200 is overlapped on the body 1100.

In the lower bed member 1200, a lower line for supplying power to the heating element 1224 is branched into a line for the lower bed upper terminal part 1210 and a line for the lower bed lower terminal part 1230.

Therefore, when the lower bed upper terminal part 1210 is in contact with the body terminal part 1600, a current flows to the lower power terminal 1232 of the lower bed lower terminal part 1230, and even when the lower bed lower terminal part 1230 is in contact with the body terminal part 1600, the current flows to the lower bed upper terminal part 1210.

Due to such structural characteristics, when the lower bed upper terminal part 1210 is in contact with the body terminal part 1600, the lower bed member 1200 is unfolded, and thus the lower bed lower terminal part 1230 is exposed to a position that may be in contact with hands of a patient or a child, whereby there is a risk of an electric shock accident. When the lower bed lower terminal part 1230 is in contact with the body terminal part 1600, the lower bed member 1200 is overlapped on the body 1100, and thus the lower bed upper terminal part 1210 is located at a position that cannot come in contact with hands of a patient or a child, whereby there is no risk of an electric shock accident.

Therefore, according to the present invention, when the lower bed upper terminal part 1210 is in contact with the body terminal part 1600, the limit switch 1218 is operated so as to cut off the current flowing to the lower bed lower terminal part 1230, thereby preventing the safety accident with respect to a patient or a child.

While the present invention has been described in detail, it should be understood that various changes, substitutions and alterations can be made hereto without departing from the spirit and scope of the invention as defined by the appended claims.

INDUSTRIAL APPLICABILITY

According to the present invention, when the apparatus for thermo-therapeutic treatment is not used, the lower bed member is slid to be overlapped on the body, thereby enhancing space occupancy, and when the apparatus for thermo-therapeutic treatment is used, the lower bed member can be easily unfolded in a sliding manner.

The invention claimed is:
1. A sliding-type apparatus for thermo-therapeutic treatment, comprising:
   a body (1100) in which a thermo-therapeutic treatment device (1010) is disposed;
   a lower bed member (1200) comprising a flat cover (1250) which is slidable on the body (1100), wherein sliding out the lower bed member (1200) extends a length of the body (1100) and exposes the thermo-therapeutic treatment device (1010) disposed in the body (1100), and wherein having been slid in, the lower bed member (1200) overlaps and covers the thermo-therapeutic treatment device (1010) disposed in the body (1100);
   a guide groove formed in the body (1100) for allowing the lower bed member (1200) to slide on the body (1100),
   wherein the thermo-therapeutic treatment device (1010) performs a thermo-therapeutic massage of a spine region, and
   wherein the lower bed member (1200) has a heating element formed therein.
2. The sliding-type apparatus of claim 1, wherein the lower bed member (1200) comprises frames having rear ends (1290) and the cover provided between the frames, and each of the frames is bent downward so that rear ends (1290) of the frames can rest on a ground surface.
3. The sliding-type apparatus of claim 1, wherein the lower bed member (1200) has a roller to be inserted into the guide groove.
4. The sliding-type apparatus of claim 1, wherein the guide groove is formed at one of an upper, a side, and a lower portion of the thermo-therapeutic treatment device (1010).
5. The sliding-type apparatus of claim 2, wherein one of a stepped portion, a protrusion, a concave portion and a solenoid member is formed at the guide groove or the frame.
6. The sliding-type apparatus of claim 5, wherein a bearing is provided at the guide groove or the frame.

* * * * *